US008602983B2

(12) United States Patent
Kleyman

(10) Patent No.: US 8,602,983 B2
(45) Date of Patent: Dec. 10, 2013

(54) ACCESS ASSEMBLY HAVING UNDERCUT STRUCTURE

(75) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 105 days.

(21) Appl. No.: 13/224,353

(22) Filed: Sep. 2, 2011

(65) Prior Publication Data

US 2012/0157785 A1 Jun. 21, 2012

Related U.S. Application Data

(60) Provisional application No. 61/424,938, filed on Dec. 20, 2010.

(51) Int. Cl.
*A61B 1/32* (2006.01)

(52) U.S. Cl.
USPC .................................................. 600/208

(58) Field of Classification Search
USPC ............. 600/204, 206, 184, 207, 208, 215; 604/24, 164.01, 167.05, 174; 606/185, 606/213
See application file for complete search history.

(56) References Cited

U.S. PATENT DOCUMENTS

| | | |
|---|---|---|
| 3,402,710 A | 9/1968 | Paleschuck |
| 3,777,757 A | 12/1973 | Gray et al. |
| 4,112,932 A | 9/1978 | Chiulli |
| 5,269,772 A | 12/1993 | Wilk |
| 5,312,417 A | 5/1994 | Wilk |
| 5,342,385 A | 8/1994 | Norelli et al. |
| 5,391,156 A | 2/1995 | Hildwein et al. |
| 5,395,367 A | 3/1995 | Wilk |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,524,644 A | 6/1996 | Crook |
| 5,545,150 A | 8/1996 | Danks et al. |
| 5,634,911 A | 6/1997 | Hermann et al. |
| 5,634,937 A | 6/1997 | Millenauer et al. |
| 5,803,921 A | 9/1998 | Bonadio |
| 5,830,191 A | 11/1998 | Hildwein et al. |
| 5,833,603 A | 11/1998 | Kovacs et al. |

(Continued)

FOREIGN PATENT DOCUMENTS

| | | |
|---|---|---|
| CA | 2702419 | 11/2010 |
| EP | 1 312 318 | 5/2003 |

(Continued)

OTHER PUBLICATIONS

European Search Report for corresponding EP11194126 date of mailing is May 2, 2012 (7 pgs).

(Continued)

*Primary Examiner* — Pedro Philogene

(57) ABSTRACT

An assembly for accessing a body cavity is provided. The access assembly includes a flexible outer sleeve configured to be received through an opening in tissue. The outer sleeve defines a passageway therethrough and a notch formed about an inner surface thereof. The access assembly further includes a support plate configured for selective reception through the passageway of the outer sleeve and within the notch formed in the inner surface. The support plate defines at least a first opening configured to receive a surgical instrument therethrough.

13 Claims, 5 Drawing Sheets

(56) References Cited

U.S. PATENT DOCUMENTS

| | | | |
|---|---|---|---|
| 5,904,703 A | 5/1999 | Gilson | |
| 5,906,577 A | 5/1999 | Beane et al. | |
| 5,911,757 A | 6/1999 | Seare, Jr. | |
| 5,990,382 A * | 11/1999 | Fox | 623/16.11 |
| 6,004,303 A | 12/1999 | Peterson | |
| 6,033,426 A * | 3/2000 | Kaji | 606/213 |
| 6,048,309 A | 4/2000 | Flom et al. | |
| 6,440,063 B1 | 8/2002 | Beane et al. | |
| 6,486,588 B2 | 11/2002 | Doron et al. | |
| 6,551,270 B1 | 4/2003 | Bimbo et al. | |
| 6,562,022 B2 | 5/2003 | Hoste et al. | |
| 6,578,577 B2 | 6/2003 | Bonadio et al. | |
| 6,723,088 B2 | 4/2004 | Gaskill, III et al. | |
| 6,929,637 B2 | 8/2005 | Gonzalez et al. | |
| 7,008,377 B2 | 3/2006 | Beane et al. | |
| 7,011,645 B2 | 3/2006 | McGuckin, Jr. et al. | |
| 7,052,454 B2 | 5/2006 | Taylor | |
| 7,125,382 B2 | 10/2006 | Zhou et al. | |
| 7,297,112 B2 | 11/2007 | Zhou et al. | |
| 7,300,399 B2 | 11/2007 | Bonadio et al. | |
| 7,416,530 B2 | 8/2008 | Turner et al. | |
| 7,473,221 B2 | 1/2009 | Ewers et al. | |
| 7,559,893 B2 | 7/2009 | Bonadio et al. | |
| 7,563,250 B2 | 7/2009 | Wenchell | |
| 7,657,297 B2 | 2/2010 | Simpson et al. | |
| 7,686,762 B1 | 3/2010 | Najafi et al. | |
| 7,758,500 B2 | 7/2010 | Boyd et al. | |
| 7,766,824 B2 | 8/2010 | Jensen et al. | |
| 7,787,963 B2 | 8/2010 | Geistert et al. | |
| 7,798,998 B2 | 9/2010 | Thompson et al. | |
| 8,157,786 B2 | 4/2012 | Miller et al. | |
| 8,187,177 B2 | 5/2012 | Kahle et al. | |
| 8,187,178 B2 | 5/2012 | Bonadio et al. | |
| 8,343,047 B2 * | 1/2013 | Albrecht et al. | 600/206 |
| 8,353,824 B2 * | 1/2013 | Shelton, IV et al. | 600/208 |
| 2002/0019635 A1 | 2/2002 | Wenstrom, Jr. et al. | |
| 2003/0014076 A1 | 1/2003 | Mollenauer et al. | |
| 2003/0093104 A1 | 5/2003 | Bonner et al. | |
| 2004/0092795 A1 | 5/2004 | Bonadio et al. | |
| 2004/0236192 A1 | 11/2004 | Nicola Shehada et al. | |
| 2005/0004478 A1 | 1/2005 | Fitz | |
| 2005/0096695 A1 | 5/2005 | Olich | |
| 2005/0165317 A1 | 7/2005 | Turner et al. | |
| 2006/0020241 A1 | 1/2006 | Piskun et al. | |
| 2006/0149306 A1 | 7/2006 | Hart et al. | |
| 2006/0161049 A1 | 7/2006 | Beane et al. | |
| 2006/0200012 A1 | 9/2006 | Mansour et al. | |
| 2006/0200220 A1 | 9/2006 | Brown et al. | |
| 2006/0247500 A1 | 11/2006 | Voegele et al. | |
| 2006/0247516 A1 | 11/2006 | Hess et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2007/0027371 A1 | 2/2007 | Benaron et al. | |
| 2007/0060884 A1 | 3/2007 | Hayek | |
| 2008/0027476 A1 | 1/2008 | Piskun | |
| 2008/0033273 A1 | 2/2008 | Zhou et al. | |
| 2008/0058652 A1 | 3/2008 | Payne | |
| 2008/0058728 A1 | 3/2008 | Soltz et al. | |
| 2008/0097332 A1 | 4/2008 | Greenhalgh et al. | |
| 2008/0108885 A1 | 5/2008 | Colvin, Jr. | |
| 2008/0154101 A1 | 6/2008 | Jain et al. | |
| 2008/0161826 A1 | 7/2008 | Guiraudon | |
| 2008/0255519 A1 | 10/2008 | Piskun et al. | |
| 2008/0287788 A1 | 11/2008 | Richardson et al. | |
| 2009/0054908 A1 | 2/2009 | Zand et al. | |
| 2009/0093752 A1 | 4/2009 | Richard et al. | |
| 2009/0093850 A1 | 4/2009 | Richard | |
| 2009/0163782 A1 | 6/2009 | Shehada et al. | |
| 2009/0209969 A1 | 8/2009 | Wolfe | |
| 2009/0299153 A1 | 12/2009 | Gerber et al. | |
| 2010/0063452 A1 | 3/2010 | Edelman et al. | |
| 2010/0081895 A1 | 4/2010 | Zand | |
| 2010/0100043 A1 | 4/2010 | Racenet | |
| 2010/0240960 A1 | 9/2010 | Richard | |
| 2010/0249523 A1 | 9/2010 | Spiegal et al. | |
| 2010/0249524 A1 | 9/2010 | Ransden et al. | |
| 2010/0280326 A1 | 11/2010 | Hess et al. | |
| 2010/0286484 A1 | 11/2010 | Stellon et al. | |
| 2010/0298646 A1 | 11/2010 | Stellon et al. | |
| 2010/0312063 A1 * | 12/2010 | Hess et al. | 600/204 |
| 2011/0028891 A1 | 2/2011 | Okoniewski | |
| 2011/0034778 A1 | 2/2011 | Kleyman | |
| 2011/0054257 A1 | 3/2011 | Stopek | |
| 2011/0054258 A1 | 3/2011 | O'Keefe et al. | |
| 2011/0054260 A1 | 3/2011 | Albrecht et al. | |
| 2011/0082341 A1 | 4/2011 | Kleyman et al. | |
| 2011/0082343 A1 | 4/2011 | Okoniewski | |
| 2011/0082346 A1 | 4/2011 | Stopek | |
| 2011/0125186 A1 | 5/2011 | Fowler et al. | |
| 2011/0166423 A1 | 7/2011 | Farascioni et al. | |

FOREIGN PATENT DOCUMENTS

| | | |
|---|---|---|
| EP | 1312318 | 5/2003 |
| EP | 2 044 889 | 4/2009 |
| EP | 2 095 781 | 9/2009 |
| EP | 2 098 182 | 9/2009 |
| EP | 2 229 900 | 9/2010 |
| EP | 2226025 | 9/2010 |
| EP | 2229900 | 9/2010 |
| EP | 2 238 924 | 10/2010 |
| EP | 2 238 925 | 10/2010 |
| EP | 2 248 478 | 11/2010 |
| EP | 2 253 283 | 11/2010 |
| EP | 2253283 | 11/2010 |
| EP | 2 272 450 | 1/2011 |
| EP | 2 292 165 | 3/2011 |
| WO | WO 93/14801 | 8/1993 |
| WO | WO2004/054456 | 7/2004 |
| WO | WO 2008/121294 | 10/2008 |
| WO | WO2010/141409 | 12/2010 |
| WO | WO 2010/141409 A1 | 12/2010 |

OTHER PUBLICATIONS

European Search Report 11194126.6-2310 dated Feb. 5, 2012.
European Search Report 11250792.6-2310 dated Feb. 24, 2012.

* cited by examiner

ACCESS ASSEMBLY HAVING UNDERCUT STRUCTURE

CROSS REFERENCE TO RELATED APPLICATION

The present application claims the benefit of and priority to U.S. Provisional Application Ser. No. 61/424,938 filed on Dec. 20, 2010, the entire contents of which are incorporated herein by reference.

BACKGROUND

1. Technical Field

The present disclosure relates to access assemblies for use in surgical procedures. More particularly, the present disclosure relates to access assemblies having an undercut structure.

2. Background of Related Art

Access assemblies configured for reception through an opening or incision into a body cavity are known, as are methods of inserting the access assemblies therethrough. Traditionally, access assemblies include a rigid cannula that is received through the tissue of the body wall into the body cavity. Endoscopic, laparoscopic and other suitable instruments may then be directed through a housing located on the proximal end of the cannula to access the body cavity in a sealing manner.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, e.g., forceps. Compression of the assembly reduces the profile of the assembly, thereby facilitating reception of the assembly into the incision. Upon release of the compressive force, the compressed assembly returns to an uncompressed configuration.

During application of a compressive force to the compressive access assemblies, whether by hand or using an insertion device, excessive handling may damage the assembly. Additionally, maintaining the compressive force on the access assembly during installation and reapplying the compressive force during removal of the access assembly may result in damage to surrounding tissue.

Therefore, it is desirable to provide an access assembly which is capable of being received through an opening and removed therefrom with limited compressive force.

SUMMARY

An assembly for accessing a body cavity is provided. The access assembly includes a flexible outer sleeve configured to be received through an opening in tissue. The outer sleeve defines a passageway therethrough and a notch formed about an inner surface thereof. The access assembly further includes a support plate configured for selective reception through the passageway of the outer sleeve and within the notch formed in the inner surface. The support plate defines at least a first opening configured to receive a surgical instrument therethrough. The opening in the tissue may be an incision or a natural orifice.

In one embodiment, the outer sleeve is composed of at least one of silicone, thermoplastic elastomers (TPE), rubber, foam, gel. The support plate may include multiple openings. The access assembly may further include a first cannula extending from the first opening in the support plate. The first cannula may be selectively secured within the first opening in the support plate. The first cannula may include a valve assembly. The valve assembly may include a valve member. The support plate may be rotatable relative to the outer sleeve when the support plate is operably received within the notch formed in the outer sleeve.

Also provided is a method of accessing a body cavity. The method includes the steps of providing an access assembly having an outer sleeve and a support plate, flexing the outer sleeve to permit reception of the outer sleeve through an opening in tissue, inserting the compressed outer sleeve through tissue, permitting the compressed outer sleeve to decompress within the opening, inserting the support plate into the outer sleeve to cause unflexing of the outer sleeve and to create a seal within the opening, and manipulating one or more instruments through the access assembly to complete a procedure. The method may further include the step of creating an incision in tissue for access to the body cavity.

DESCRIPTION OF THE DRAWINGS

Embodiments of a flexible access assembly are disclosed herein with reference to the drawings, wherein.

DETAILED DESCRIPTION

Embodiments of the presently disclosed access assembly will now be described in detail with reference to the drawings wherein like numerals designate identical or corresponding elements in each of the several views. As is common in the art, the term "proximal" refers to that part or component closer to the user or operator, e.g. surgeon or physician, while the term "distal" refers to that part or component further away from the user. Although the access assemblies of the present disclosure will be described as relates to accessing an abdominal cavity through an incision in the abdominal wall, the access assemblies of the present disclosure may be modified for use in other closed procedures, e.g., laparoscopic, arthroscopic, endoscopic. Furthermore, the access assemblies of the present disclosure may be modified for use in accessing internal cavities through natural orifices, e.g., anus, vagina.

Figure 1:
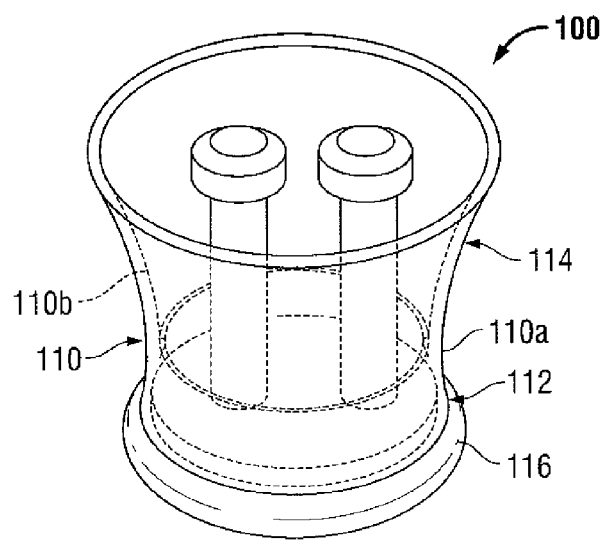
FIG. 1 is a perspective view of an embodiment of an access assembly according to the present disclosure.

Referring initially to FIG. 1, an access assembly according to an embodiment of the present disclosure is shown generally as access assembly 100. Access assembly 100 is configured for insertion through an opening in tissue, e.g., an incision, such that after insertion, access assembly 100 creates a seal within the opening through which a surgeon may insert and manipulate one or more surgical instruments to complete a procedure.

Figure 2:
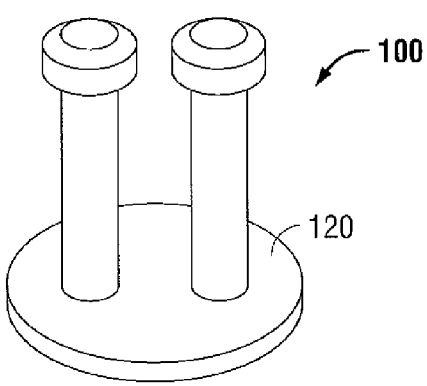
FIG. 2 is an exploded perspective view of the access assembly of FIG. 1.
Figure 2:
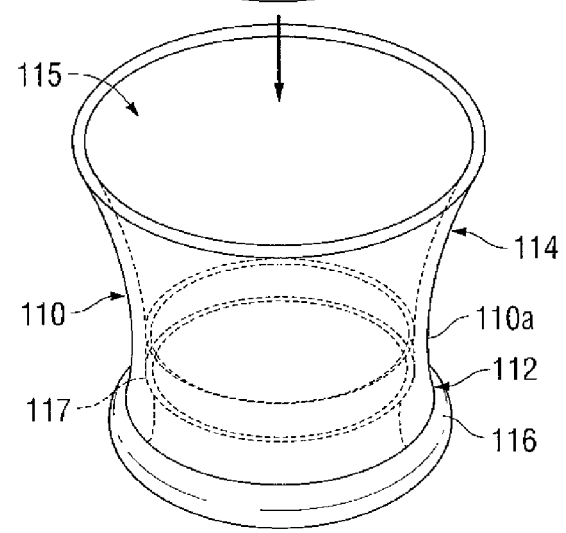
Figure 3:
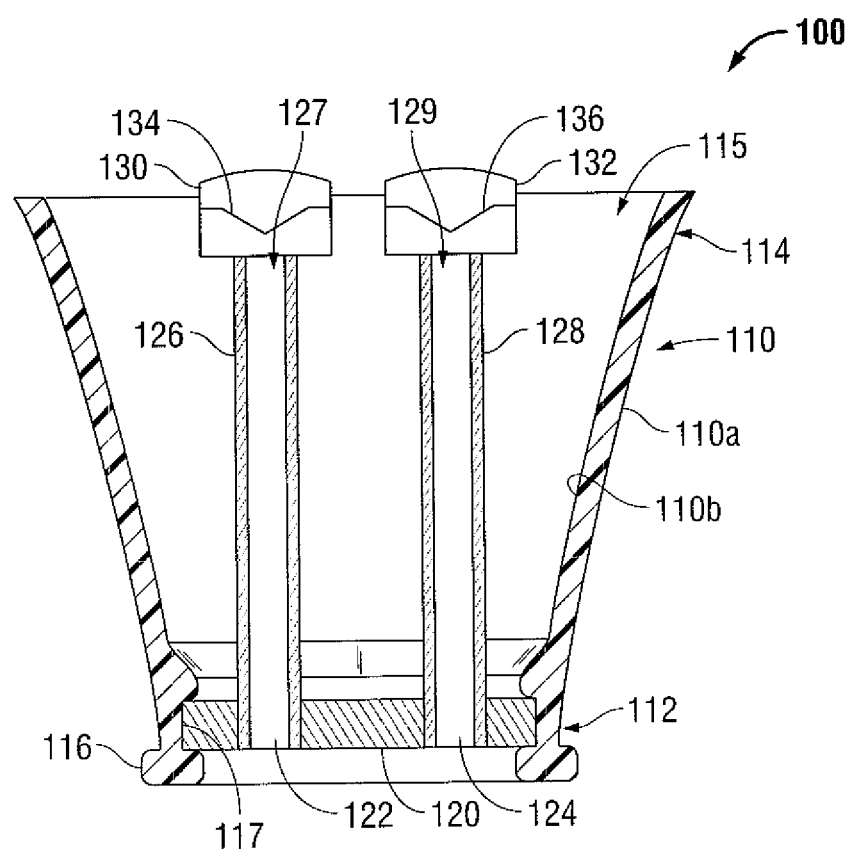
FIG. 3 is a cross-sectional side view of the access assembly of FIGS. 1 and 2.

With reference to FIGS. 1-3, access assembly 100 includes an outer tissue seal or sleeve 110 and an inner support plate or disk 120. Sleeve 110 and support disk 120 may be formed of various materials, such as, for example, silicone, thermoplastic elastomers (TPE), rubber, foam, gel, etc. Sleeve 110 and support plate 120 may be constructed from the same or different materials. In one embodiment, sleeve 110 is formed of a TPE material that is infused with an inert gas, e.g. $CO_2$ or Nitrogen, to form a foam structure, and inner support plate 120 is formed of a substantially rigid thermoplastic elastomer, to form a substantially solid support structure.

Figure 5:
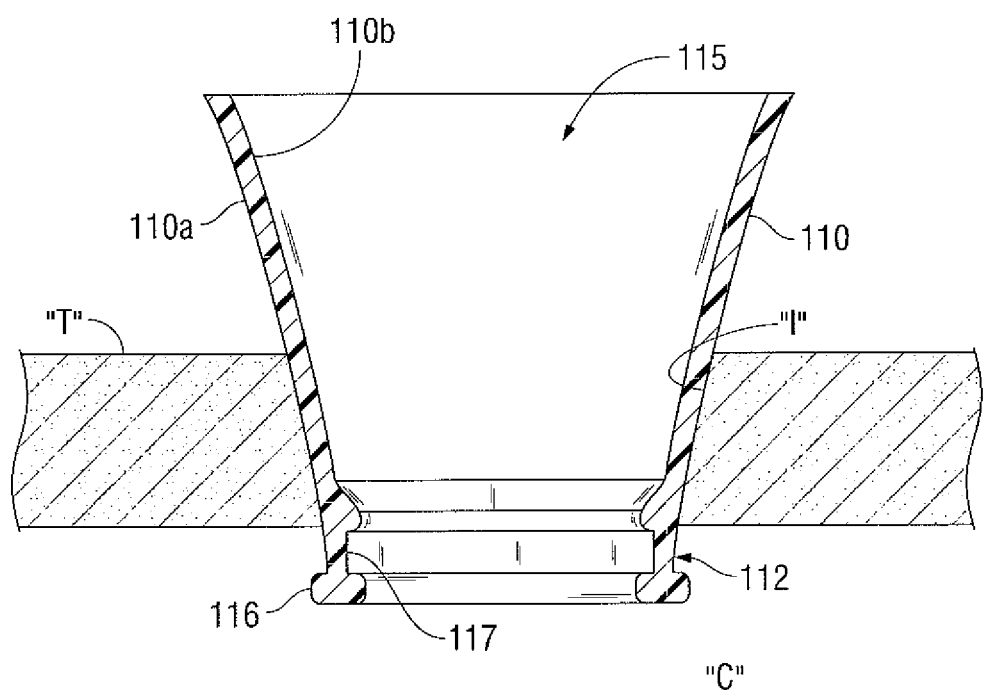
FIG. 5 is a cross-sectional side view of the outer sleeve of FIG. 4, received through an incision in tissue.

Still referring to FIGS. 1-3, an outer surface 110a of sleeve 110 may be coated with a lubricant, e.g. Parylene N or C, in order to create a lubricious surface and facilitate insertion of sleeve 110 into an incision "I" (FIG. 5). Outer sleeve additionally, or in the alternative, may be textured or may include a textured coating (not shown) for facilitating engagement with tissue "T" about incision "I". Various other coatings, e.g., hydrophilic, hydrophobic, bio-agents, anti-infection, analgesic, may also be employed to improve the characteristics of access assembly 100 or to adapt access assembly 100 for a specific procedure. Optionally, outer sleeve 110 may include a protective outer layer (not shown). An inner surface 110b of sleeve 110 may be coated with a lubricant to facilitate insertion of support plate 120 therein.

With particular reference now to FIGS. 2 and 3, sleeve 110 of access assembly 100 defines a curved outer surface having open first and second ends 112, 114. First end 112 of outer sleeve 110 is configured to be received within a body cavity "C" (FIG. 5) of a patient. Although shown including having a circular cross-sectional profile, it is envisioned that outer sleeve 110 may include other cross-sectional profiles, including oval. A rim or flange 116 is formed on first end 112 of outer sleeve 110 about outer surface 110a thereof. Although shown formed extending completely about outer surface 110a of outer sleeve 110, rim 116 may extend only partially and/or intermittently about outer surface 110a of outer sleeve 110. Second end 114 of outer sleeve 110 is flared outwardly and is configured to be maintained external of incision "I". In one embodiment, flared second end 114 delineates the boundary through which an instrument (not shown) inserted through access port 100 may be manipulated without compromising the integrity of the seal between access assembly 100 and tissue "T", between outer sleeve 110 and support plate 120, and/or between support plate 120 and the instrument. Rim 116 on first end 112 and flared second end 114 of outer sleeve 110 aid in preventing longitudinal movement of access assembly 100 through incision "I" upon receipt of access assembly 100 within incision "I".

As the thickness of tissue "T" depends on the body composition of the patient and the location through which the underlying cavity is being accessed, the length and size of access assembly 100, generally, and outer sleeve 110, specifically, may be modified to suit a given procedure. In this manner, an adult patient having fatty abdominal tissue may require an access assembly 100 having a greater distance between first and second ends 112, 114 then an access assembly sized for a child. The flared configuration of second end 114 enables access assembly 100 to be used on tissue ranging thickness. It is envisioned that second end 114 of access assembly 100 may be configured for shortening by a clinician prior to or during a procedure in the event outer sleeve 110 exceeds a necessary length.

With reference still to FIGS. 2 and 3, outer sleeve 110 defines a longitudinal opening 115 extending therethrough. As shown, longitudinal opening 115 includes a curved-tapered shape corresponding to the shape of outer sleeve 110. Alternatively, opening 115 may be conical, stepped or otherwise configured to facilitate reception of support plate 120 therein and passage of one or more instruments therethrough. Outer sleeve 110 further includes an undercut structure defining a notch 117 about inner surface 110b on first end 112. Notch 117 is configured to selectively receive support plate 120 therein. Notch 117 may extend about the entire inner surface of first end 112. Alternatively, notch 117 may extend only partially and/or intermittently about the inner surface of first end 112. As seen in FIG. 5, notch 117 is positioned near first end 112 of outer sleeve 110 such that when outer sleeve 110 is received through incision "I", support plate 120 is positioned within body cavity "C". In other words, support plate 120 is positioned below tissue "T" when access assembly 100 is properly positioned within incision "I". However, it is envisioned that sleeve 110 may be configured such that notch 117, and thereby, support plate 120, are positioned in horizontal alignment with tissue "T", or alternatively, above of tissue "T".

Still referring to FIGS. 2 and 3, support plate 120 of access assembly 100 includes a cylindrical, substantially rigid body configured to be received through longitudinal opening 115 of sleeve 110 and within notch 117. As shown, support plate 120 is substantially planar and includes a circular profile to correspond with the circular cross-sectional profile of outer sleeve 110, however, it is envisioned that support plate 120 may be formed of varying thickness and may include a profile configured to correspond with an outer sleeve of an alternative configuration. Support plate 120 is configured to be selectively received within notch 117. In one embodiment, support plate 120 is configured to be rotatable within notch 117. In this manner, one or more surgical devices "D1", "D2", inserted therethrough, may be further manipulated during a procedure.

Support plate 120 defines a pair of openings 122, 124. Cannulas 126, 128 extend from openings 122, 124, respectively. As shown, cannulas 126, 128 are securely affixed within respective openings 122, 124. In some embodiments, cannulas 126, 128 are configured to be selectively secured within openings 122, 124, respectively. For example, openings 122, 124 may include a threaded proximal portion configured to engage threaded ends (not shown) of cannula 126, 128, respectively. In this manner, the configuration of the cannulas used during a procedure may be selected and/or interchanged by a clinician up to and during a procedure. Cannulas 126, 128 may be replaced or interchanged during a procedure to satisfy the requirements of the procedure. In an alternative embodiment, 126, 128 cannulas are integrally formed with support plate 120.

Cannulas 126, 128 each define a longitudinal passageway 127, 129, respectively, extending therethrough. Each of cannulas 126, 128 may include a valve housing 130, 132, respectively. Each of valve housings 130, 132 may include a valve member 134, 136, respectively. Each of valve members 134, 136 are configured to seal respective passageways 127, 129 of cannulas 126, 128, respectively, in the absence of a surgical device "D1", "D2" (FIG. 6) inserted therethrough. Each of cannulas 126, 128 and valve housings 130, 132 may have the same configuration for receiving instruments of similar configuration. Alternatively, the configurations of cannulas 126, 128 and valve housings 130, 132, respectively, may differ. Although shown including two (2) cannulas, 126, 128, it is envisioned that support plate 120 may be provided without a cannula (FIG. 8), with only a single cannula or with three (3) or more cannulas.

The use of access assembly 100 will now be described with reference to FIGS. 4-6. Although the following discussion will include using access assembly 100 for accessing a body cavity "C" through an incision "I", as discussed above, access assembly 100 may be used for accessing other cavities or lumen through other openings, including naturally occurring orifices, e.g., anus. Initially, an incision "I" (FIG. 5) is created in tissue "T" through which access assembly 100 will be inserted to access body cavity "C".

Figure 4:
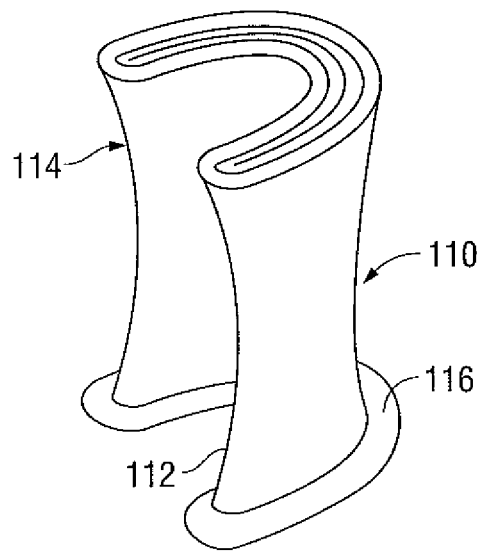
FIG. 4 is a perspective view of the outer sleeve of the access assembly of FIGS. 1-3, in a collapsed configuration.

With reference to FIG. 4, support plate 120 is removed from outer sleeve 110 in the event that outer sleeve 110 and support plate 120 are not provided separate from each other. Once separated, outer sleeve 110 is radially and/or laterally compressed and/or folded to reduce the cross-section profile of outer sleeve 110 and to facilitate insertion of first end 112 of outer sleeve 110 through incision "I".

Turning to FIG. 5, once first end 112 of outer sleeve 110 is received through incision "I" such that rim 116 is received within body cavity "C", outer sleeve 110 is permitted to return to an initial, uncompressed condition. Outer sleeve 110 may only partially decompress within incision "I" because of the force of tissue "T" against outer sleeve 110. Support plate 120 is then inserted within passageway 115 of outer sleeve 110 as outer sleeve 110 is maintained within incision "I" in tissue "T".

Figure 6:
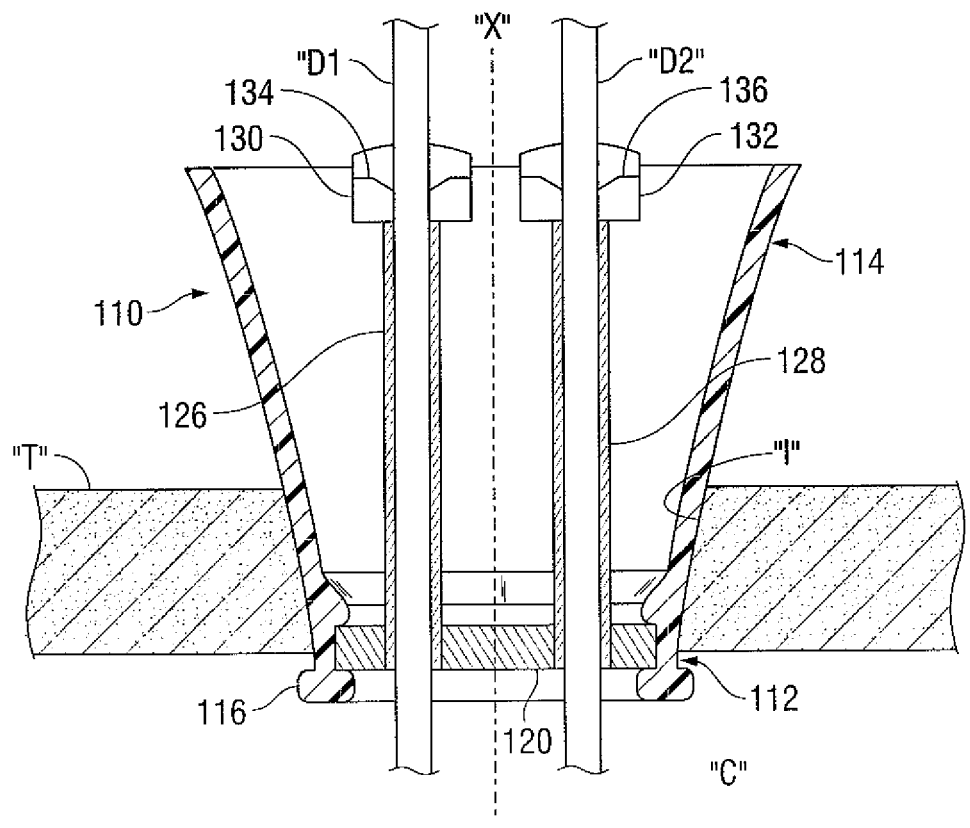
FIG. 6 is a cross-sectional side view of the outer sleeve of FIGS. 4 and 5 received through the incision and further including a support plate of the access assembly of FIGS. 1-3 received therein.

With reference to FIG. 6, insertion of support plate 120 within outer sleeve 110 causes outer sleeve 110 to return to the initial, uncompressed and/or unfolded condition. Decompression or expansion of outer sleeve 110 creates a seal between outer sleeve 110 and tissue "T" to prevent the escape of insufflation gas through incision "I". As discussed above, outer sleeve 110 and support plate 120 are also configured to form a seal therebetween to prevent the escape of insufflation gas from body cavity "C".

With reference still to FIG. 6, once support plate 120 is received with outer sleeve 110, access assembly 100 operates in a traditional manner. Each of cannula 126, 128 are configured to selectively receive one or more surgical devices "D1", "D2". During a procedure, it is envisioned that support plate 120 may be separated from outer sleeve 110 to permit the removal of an organ or other tissue therethrough. Removal of support plate 120 further permits the passage of larger instruments into cavity "C" through access assembly 100. While positioned through incision "I" in tissue "T", access assembly 100 may be used to complete any number of procedures.

Removal of access assembly 100 from within incision "I" occurs in the reverse order of insertion. Initially, support plate 120 is separated from outer sleeve 110. Outer sleeve 110 is then compressed to permit retraction from incision "I". Alternatively, both inner core 120 and outer sleeve 110 may be compressed simultaneously such that access assembly 100 may be removed as a single unit. Once access assembly 100 is removed from incision "I", incision "I" is closed in a conventional manner.

Figure 7:
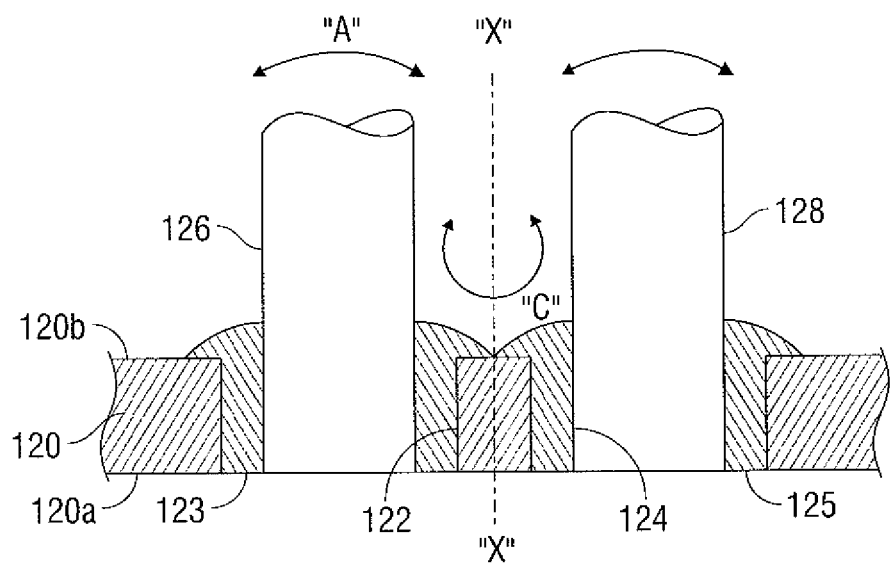
FIG. 7 is an enlarged partial view of a support plate according to an alternative embodiment of the present disclosure.

Turning now to FIG. 7, in an alternative embodiment, support plate 120 defines a pair of openings 122, 124. Operably engaged within each opening 122, 124 is a respective insert 123, 125. Inserts 123, 125 may be securely affixed with openings 122, 124 using adhesive, welding, bonding or other suitable means. Alternatively, inserts 123, 125 may be selectively received within openings 122, 124. In one embodiment, inserts 123, 125 include proximal and distal flanges (not shown) configured for selectively engaging inner and outer surfaces 120a, 120b of support plate 120. Inserts 123, 125 are formed of a material that permits movement of cannulas 126, 128, respectively, relative to support plate 120, as indicated by arrows "A", "B", respectively. Inserts 123, 125 are further configured to form a seal between support plate 120 and cannulas 126, 128. Cannulas 126, 128 may be securely affixed to inserts 123, 125. Alternatively, cannulas 126, 128 are selectively positionable and/or removable from inserts 123, 125. In this manner, cannulas 126, 128 may be repositioned and/or replaced. Although shown with cannulas 126, 128 received through respective inserts 123, 125, it is envisioned that inserts 123, 125 may instead be configured to receive one or more instruments therethrough. In this manner, inserts 123, 125 may include a seal member (not shown) for sealing respective openings 122, 124 in the absence of an instrument inserted therethrough. As discussed above, support plate 120 may be configured to be rotated within outer sleeve 110 along a longitudinal axis "x", as indicated by arrows "C".

Figure 8:
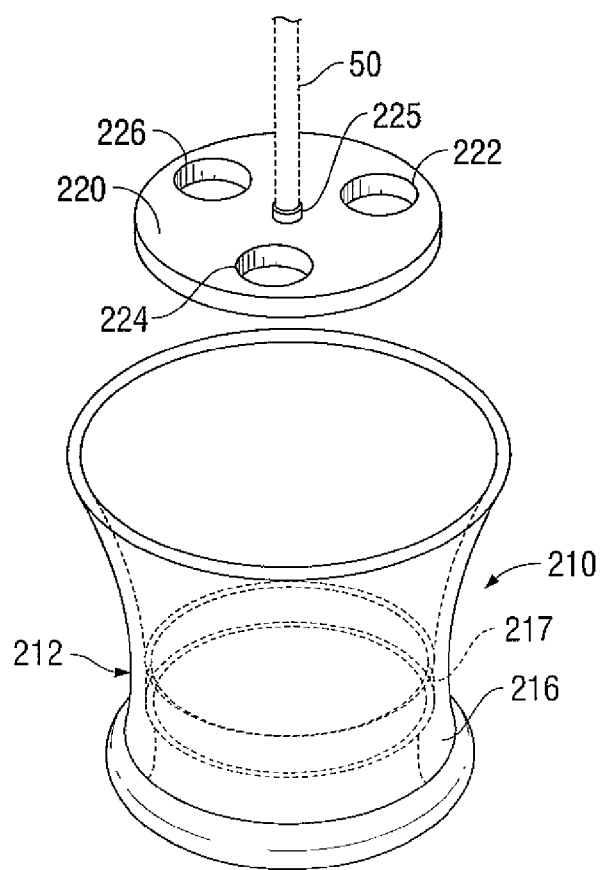
FIG. 8 is an exploded perspective view of an access assembly according to an alternative embodiment of the present disclosure.
Figure 9:
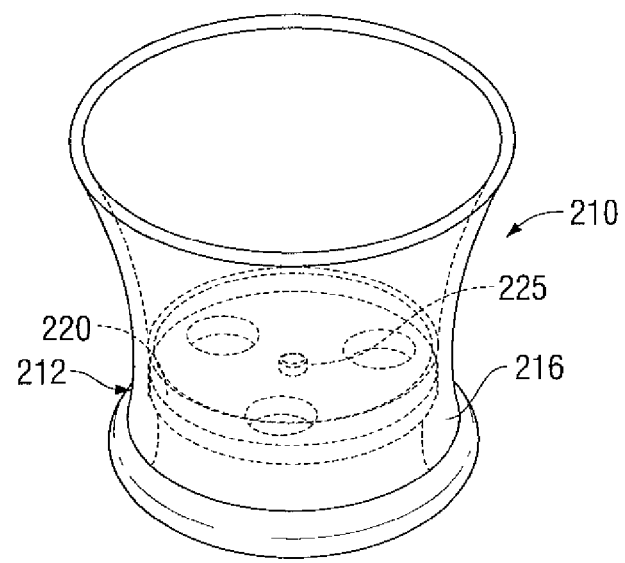
FIG. 9 is a perspective side view of the access assembly of FIG. 8.

With reference now to FIGS. 8 and 9, an alternative embodiment of an access assembly according to the present disclosure is shown generally as access assembly 200. Access assembly 200 is substantially similar to access assembly 100 described hereinabove, and will therefore only be described as relates to the differences therebetween. Access assembly 200 includes an outer sleeve 210 and a support plate 220. First end 212 of outer sleeve 210 includes a generally tapered configuration configured to be received through an incision "I". First end 212 includes an undercut structure defining a notch 217. First end 212 further includes a flange portion 216.

As seen in FIG. 8, in a first or initial condition, e.g., in the absence of support plate 220, flange portion 216 extends radially inward. In this manner, first end 212 of outer sleeve 210 is configured for ease of reception within an incision "I". As seen in FIG. 9, in a second condition, e.g., upon receipt of support plate 220 therein, outer sleeve 210 is configured such that flange portion 216 and first end 212 thereof flare radially outward. In this manner, flange portion 216 aids in preventing longitudinal movement or retraction of access assembly 200 through incision "I" upon receipt of access assembly 200 within incision "I".

With reference still to FIG. 8, support plate 220 includes a plurality of openings 222, 224, 226. Each of openings 222, 224, 226 may include a cannula (not shown) and/or an insert (not shown), as discussed above. Alternatively, openings 222, 224, 226 may be left open. Support plate 220 includes a tab 225 or other suitable structure configured to selectively engage an insertion device 50. Insertion device 50 may be selectively attached to support plate 220 to facilitate insertion of support plate 220 within notch 217 of outer sleeve 210. Separation of insertion device 50 from tab 225 creates spaces within outer sleeve 210 for greater manipulation of instruments inserted through openings 222, 224, 226.

It will be understood that various modifications may be made to the embodiments disclosed herein. For example, the support plate may form an annular member having a single opening therethrough to facilitate passage of an oversized surgical device therethrough. Therefore, the above description should not be construed as limiting, but merely as exemplifications of particular embodiments. Those skilled in the art will envision other modifications within the scope and spirit of the claims appended hereto.

The invention claimed is:
1. An access assembly comprising:
a flexible outer sleeve configured to be received through an opening in tissue while in a compressed condition, the outer sleeve defining a passageway therethrough and a notch formed about an inner surface thereof; and a rigid support plate configured for selective reception through the passageway of the outer sleeve and within the notch formed in the inner surface, the support plate defining at least a first opening configured to receive a surgical instrument therethrough, wherein the support plate causes the flexible outer sleeve to transition from the compressed condition to an uncompressed condition and create a seal between the flexible outer sleeve and the opening in tissue when the support plate is received within the notch.

2. The access assembly of claim 1, wherein the outer sleeve is composed of at least one of silicone, thermoplastic elastomers (TPE), rubber, foam, gel.

3. The access assembly of claim 1, wherein the support plate includes multiple openings.

4. The access assembly of claim 1, wherein the support plate includes three openings.

5. The access assembly of claim 1, further including a first cannula extending from the first opening in the support plate.

6. The access assembly of claim 5, wherein the first cannula is selectively secured within the first opening in the support plate.

7. The access assembly of claim 5, wherein the first cannula includes a valve assembly.

8. The access assembly of claim 7, wherein the valve assembly includes a valve member.

9. The access assembly of claim 1, wherein the opening in the tissue is an incision.

10. The access assembly of claim 1, wherein the opening in tissue is a natural orifice.

11. The access assembly of claim 1, wherein the support plate is rotatable relative to the outer sleeve when the support plate is operably received within the notch formed in the outer sleeve.

12. A method of accessing a body cavity, the method comprising the steps of:
providing an access assembly having an outer sleeve and a rigid support plate;
flexing the outer sleeve to a compressed condition to permit reception of the outer sleeve through an opening in tissue;
inserting the compressed outer sleeve through tissue;
permitting the compressed outer sleeve to decompress within the opening;
inserting the support plate into the outer sleeve to cause unflexing of the outer sleeve and to create a seal within the opening, wherein the support plate causes the flexible outer sleeve to transition from the compressed condition to an uncompressed condition when the support plate is received within the notch; and
manipulating one or more instruments through the access assembly to complete a procedure.

13. The method of claim 12, further including the step of creating an incision in tissue for access to the body cavity.

* * * * *